US00RE34044E

United States Patent [19]

Broussard

[11] E Patent Number: Re. 34,044

[45] Reissued Date of Patent: Aug. 25, 1992

[54] ADJUSTABLE ORTHODONTIC BRACKET ASSEMBLY

[76] Inventor: Garfford J. Broussard, 203 Chimney Rock, Houston, Tex. 77024

[21] Appl. No.: 550,979

[22] Filed: Jul. 9, 1990

Related U.S. Patent Documents

Reissue of:

[64] Patent No.: 4,917,602
Issued: Apr. 17, 1990
Appl. No.: 242,717
Filed: Sep. 12, 1988

[51] Int. Cl.[5] ..... A61C 3/00
[52] U.S. Cl. ..... 433/8; 433/16
[58] Field of Search ..... 433/8, 9, 10, 13, 14, 433/16

[56] References Cited

U.S. PATENT DOCUMENTS

| | | | |
|---|---|---|---|
| 3,238,619 | 3/1966 | Brunsoro et al. | 433/13 |
| 3,256,602 | 6/1966 | Broussard et al. | 32/14 |
| 4,107,844 | 8/1978 | Kurz | 32/14 A |
| 4,310,306 | 1/1982 | Wallshein | 433/14 |
| 4,350,487 | 9/1982 | Kesling et al. | 433/14 |
| 4,529,382 | 7/1985 | Creekmore | 433/9 |
| 4,597,739 | 7/1986 | Rosenberg | 433/16 |
| 4,676,746 | 6/1987 | Klapper | 433/15 |
| 4,799,882 | 2/1989 | Kesling | 433/8 |
| 4,877,398 | 10/1989 | Kesling | 433/8 |

FOREIGN PATENT DOCUMENTS

| | | | |
|---|---|---|---|
| 0379668 | 8/1990 | European Pat. Off. | 433/10 |

*Primary Examiner*—Cary E. O'Connor
*Attorney, Agent, or Firm*—Ben D. Tobor

[57] ABSTRACT

An adjustable bracket assembly for use with an arch wire includes a base member, an attachment member, and means for movably associating the base member with the attachment member, whereby the attachment member is slidably received within the base member, whereby a variable sized arch wire receiving channel may be formed.

22 Claims, 4 Drawing Sheets

FIG.6
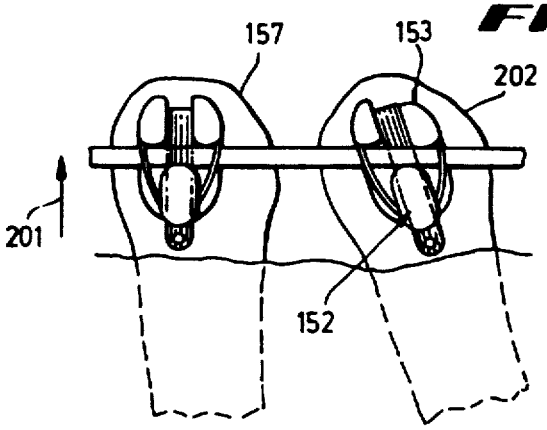
FIG.5
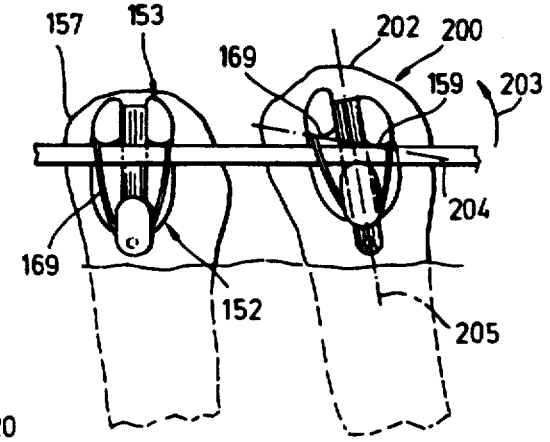
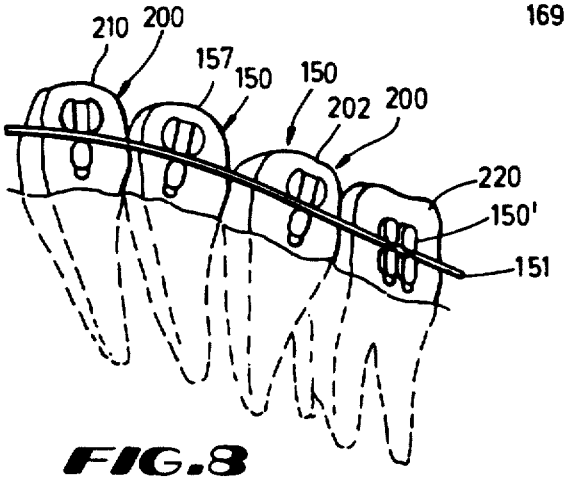
FIG.8
FIG.7
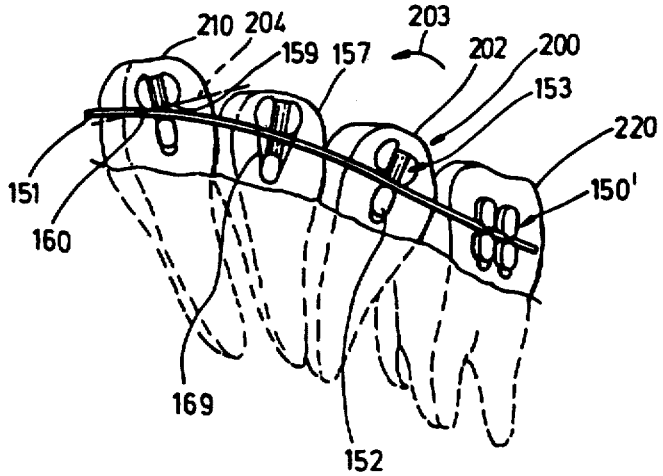

ADJUSTABLE ORTHODONTIC BRACKET ASSEMBLY

Matter enclosed in heavy brackets [ ] appears in the original patent but forms no part of this reissue specification; matter printed in italics indicates the additions made by reissue.

BACKGROUND OF THE INVENTION

1. Field of the Invention

The invention relates to an adjustable orthodontic bracket assembly, adapted for use with an arch wire, wherein different sizes of arch wire may be utilized and vector forces acting upon a tooth may be changed or varied, all without removing the bracket assembly from the tooth being treated.

2. Description of the Prior Art

In orthodontic practice, arch wire bending is a time consuming, but essential component of the treatment procedure. Tooth alignment problems are corrected by applying appropriate bends to a generally U-shaped arch wire. When out-of-line, or malposed, teeth are secured to the arch wire by means of orthodontic brackets, forces exerted upon the teeth to move them into a desired orientation over a period of time to correct malocclusions of the teeth. Teeth initially having proper alignment are secured to unbent portions of the arch wire and may serve to define an "ideal" orientation to which the other teeth are directed.

The modes of tooth movement required for correcting malocclusions of the teeth include: up-down (elevating or lowering a tooth within its socket); rotation (turning of the tooth in its socket about its longitudinal axis either clockwise or counter clockwise); tipping (tilting of the tooth toward the front, or mesially of the dental arch; or toward the back, or distally of the dental arch); and torquing (twisting, or turning, the tooth about an axis formed by the arch wire, either toward the tongue, or lingual surface of the mouth, or toward the cheek or lip, or buccal or labial surface of the mouth).

Present day orthodontic brackets are applied to the teeth by bonding the bracket directly to the teeth. Each bracket is typically provided with a slot for arch wire containment, or an arch wire receiving channel, and ligature tie grooves, or wings, to receive elastic rings, or rubber bands, or tie wires for securing the arch wire to each bracket. In older techniques, the brackets were first welded to metal bands and the metal bands were then slipped over the teeth and cemented into place. Present one-piece orthodontic brackets are cast or molded to have a fixed, predetermined amount of torque, tipping, and sometimes rotation designed into the particular bracket. These brackets are designed to limit arch wire bending somewhat for average, normally-shaped teeth, and it is assumed that the bracket will be placed and bonded in a precisely determined position upon the tooth. Since provision has only be made for "average" teeth in these fixed, one-piece bracket systems, there is typically no allowance for normally-occurring differences in tooth anatomy, or in bracket placement errors. Bending of the arch wire is therefore typically required to correct the alignment problems. In many treatments, it may be necessary to remove the brackets from the teeth, and rebond them in a different position; however, this can be a time consuming process.

It has been proposed to provide multi-piece bracket systems, which typically include a bracket and a bracket holder mounted upon the tooth, as an attempt to eliminate some arch wire bending procedures, as well as an attempt to avoid removal and rebonding of the bracket. A disadvantage of such systems has been a large initial expense because the orthodontist is required to purchase and maintain an inventory of a very large number of specially slotted brackets. Furthermore, identification of the proper bracket for each tooth and each situation is believed to be quite time consuming. It is believed that such systems also suffer from the disadvantage that it is typically necessary to remove the bracket from its holder in a mesial-distal (side-to-side) movement, a difficult operation particularly with small, closely positioned teeth. Some of these systems also required that the orthodontist insert small pin members in order to hold the multi-piece bracket systems together into their desired configuration, which can also be a difficult and time consuming task.

A major disadvantage associated with both prior art one-piece or multi-piece bracket assemblies has been that once the orthodontist begins the orthodontic treatment and selects a particular size arch wire to use, he must continue to use that particular arch wire throughout the treatment procedure. If he decides to change the size of the arch wire, it is necessary, in the case of one-piece brackets, to remove all of the brackets from the teeth, and replace them with different brackets having a larger arch wire slot, or arch wire receiving channel, in order to accommodate the larger, or smaller, size arch wire. In this regard, typically more force can be applied to the teeth when a larger arch wire is used. In the case of multi-piece bracket assemblies, it would be necessary to remove all of the brackets from the holders in order to substitute different brackets having either a larger or a smaller size slot, or arch wire receiving channel. Furthermore, in many of the single-piece brackets, and multi-piece bracket assemblies, repeated adjustments to the arch wire, and/or repeated substitution of bracket pieces is required as the treatment progresses and the malposed teeth move into their desired orientation.

An additional disadvantage associated with prior art orthodontic brackets relates to the configuration of the slot, or arch wire receiving channel. They are all typically formed as a generally U-shaped channel, having the vertically extending legs joined to the base at right angles to one another, and there are also right angles formed at the exit ends of the channel. Thus, movement of the arch wire, whether caused by sliding movement of the arch wire within the channel, or caused by bending of the arch wire by the orthodontist, can cause the arch wire to bind within the slot of the bracket at the sharp edges formed by the right angles.

Accordingly, prior to the development of the present invention, there has been no adjustable orthodontic bracket assembly adapted for use with an arch wire which: is simple and economical to use; permits different sizes of arch wires to be utilized without either removing and rebonding the bracket to the teeth or by changing all the bracket components of multi-part systems; easily permits changing the vector forces acting upon the teeth without removing the bracket or substituting an extensive number of bracket components; and prevents binding of the arch wire within the arch wire receiving channel, or slot. Therefore, the art has sought an adjustable orthodontic bracket assembly, adapted for use with an arch wire, which: is simple and economic to use; permits different sizes of arch wires to be utilized in the orthodontic treatment, without removal and rebonding of different sized brackets to the teeth, or without substituting an entirely different size set of bracket members; permits the vector forces exerted upon the teeth to be easily changed without removing and rebonding brackets to the teeth, or without substituting an excessive number of bracket components; and prevents binding of the arch wire within the arch wire receiving channel.

SUMMARY OF THE INVENTION

In accordance with the invention, the foregoing advantages have been achieved through the present adjustable bracket assembly, adapted for use with an arch wire. The present invention includes: a base member having at least one arch wire contact surface, the base member adapted to be associated with the surface of a tooth; an attachment member having at least one arch wire contact surface; and means for movably associating the base member and the attachment member with respect to one another to provide an arch wire receiving channel formed by the at least one arch wire contact surfaces of the base member and the attachment member, whereby the size of the arch wire receiving channel may be varied to accommodate various sizes of arch wire. A feature of the present invention is that the movable association means may include a sliding connection means between the base member and the attachment member, and the sliding connection means may include an opening disposed within the base member and the attachment member has an elongate support member which is received within the opening in a sliding relationship.

A further feature of the present invention is that it may include means for biasing the base member and the attachment member together to bias the at least one arch wire contact surfaces of the base member and the attachment member into engagement with the arch wire. Another feature of the present invention is that the base member and the attachment member may be magnetized to provide the biasing means, whereby the base member and the attachment member are biased toward one another by magnetic force.

Another feature of the present invention is that it may include a means for releasably locking the base member and the attachment member together while permitting the base member and the attachment member to move with respect to one another, whereby the base member and the attachment member are prevented from becoming accidentally disassociated while in use.

A further feature of the present invention is that it may include a means for tipping the tooth to which the base member is associated, the tipping means including two arch wire contact surfaces spaced apart from one another and disposed on the attachment member, the two arch wire contact surfaces lying in a plane which is not perpendicular with the longitudinal axis of the attachment, whereby the tooth may be tipped about the at least one arch wire contact surface of the base member and one contact surface of the attachment member, until both arch wire contact surfaces of the attachment member contact the arch wire.

An additional feature of the present invention is that it may be include means for rotating the tooth to which the base member is associated, the rotation means including at least one arch wire support slot disposed on the attachment member and adjacent the at least one arch wire contact surface, the arch wire support block adapted to contact the arch wire and provide a fulcrum about which the tooth is rotated.

In accordance with the invention, the foregoing advantages have also been achieved through the present method for forming a variable size arch wire receiving channel in an orthodontic bracket assembly. The present invention includes the steps of: providing at least one arch wire contact surface upon a base member; providing at least one arch wire contact surface upon an attachment member; and movably associating the base member and the attachment member with respect to one another, whereby the at least one arch wire contact surfaces of both the base member and the attachment member may contact and engage the arch wire. A further feature of the present invention is that the attachment and the base member may be movably associated with respect to one another by slidably receiving a portion of the attachment member within an opening formed in the base member.

The adjustable orthodontic bracket assembly adapted for use with an arch wire of the present invention, when compared with previously proposed prior art orthodontic brackets and bracket assemblies, has the advantages of: being simple and economical to use; permits different sizes of arch wires to be used without removal and rebonding of the brackets to the teeth; permits the vector forces applied to the teeth to be readily changed without removal and rebonding of the brackets to the teeth; and prevents binding of the arch wire within the arch wire receiving channel.

BRIEF DESCRIPTION OF THE DRAWINGS

In the Drawings:

FIG. 5 is a front view of two teeth having bracket assemblies in accordance with the present invention bonded thereon, the teeth being shown at the beginning of an orthodontic procedure;

FIG. 6 is a front view of the two teeth of FIG. 5 toward the end of the orthodontic treatment;

FIG. 7 is a perspective view of four teeth having orthodontic bracket assemblies in accordance with the present invention bonded thereon, the teeth being shown at the beginning of an orthodontic treatment;

FIG. 8 is a perspective view of the teeth of FIG. 7 toward the end of the orthodontic treatment;

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
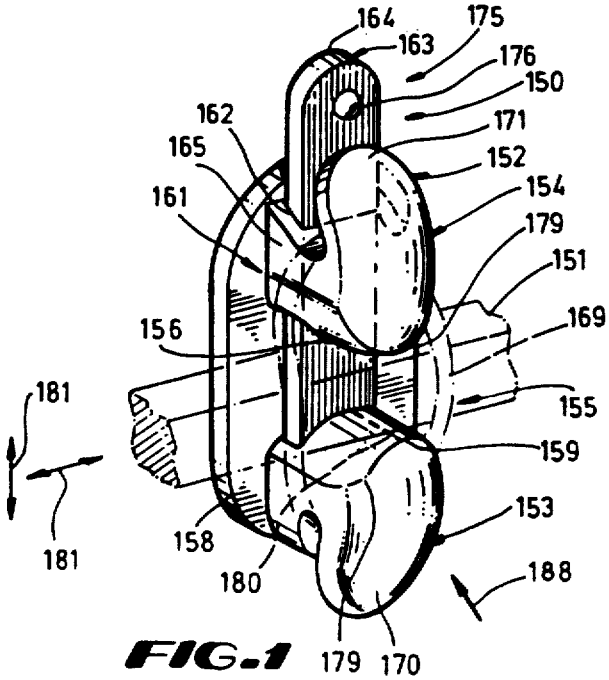
FIG. 1 is a perspective view of an adjustable orthodontic bracket assembly in accordance with the present invention.
Figure 2:
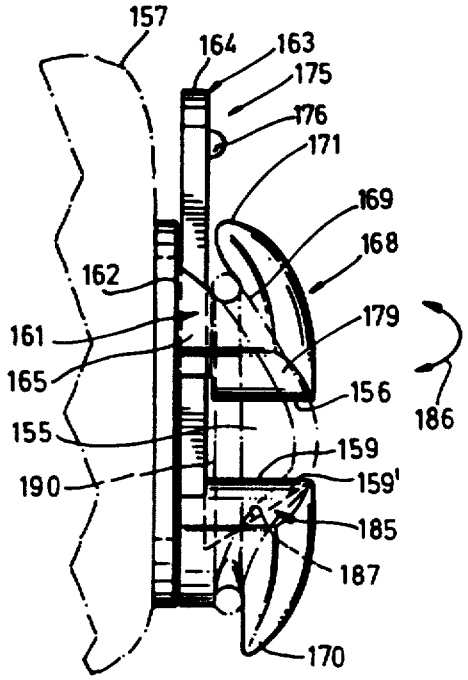
FIG. 2 is a side view of the bracket assembly of FIG. 1.
Figure 3:
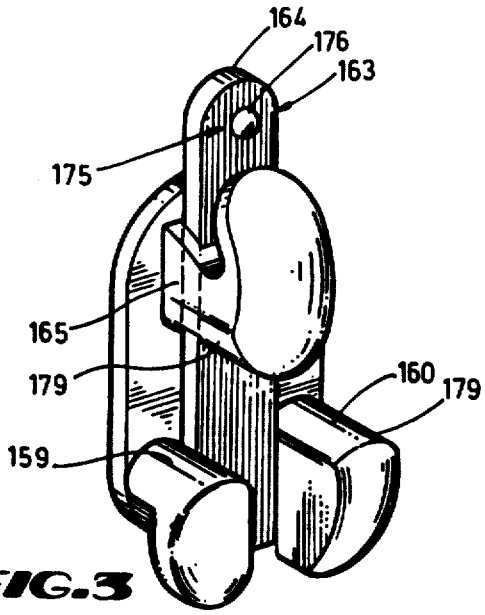
FIG. 3 is a perspective view of a bracket assembly in accordance with the present invention.

With reference to FIGS. 1-3, an adjustable orthodontic bracket assembly 150 adapted for use with an arch wire 151, in accordance with the present invention, is shown to generally comprise a base member 152; an attachment member 153; and means for movably associating 154 base member 152 and the attachment member 153 to one another to provide an arch wire receiving channel 155. Base member 152 has at least one arch wire contact surface 156 associated therewith, and the base member 152 is adapted to be associated with the surface of a tooth 157 (phantom lines in FIG. 2) in a conventional manner. In this regard, base member 152 may include a mounting base 158 with any suitable configuration which may be bonded in a conventional manner to the surface of tooth 157. Preferably, mounting base 158 has an oval configuration so as to provide smooth rounded surfaces for comfort for the wearer and for ease of cleaning. As is conventional in the art, base member 152, as well as attachment member 153, may be made from any suitable material used for orthodontic brackets and appliances, such as stainless steel or any plastic material having the requisite strength characteristics. As will hereinafter be apparent to one of ordinary skill in the art, the adjustable orthodontic bracket assembly 150 in accordance with the present invention, may also be associated with a tooth, such as tooth 157, as by securing mounting base 158 to conventional bands (not shown) which are cemented to the teeth.

Still with reference to FIGS. 1-3, attachment member 153 also has at least one arch wire contact surface 159 associated therewith. As will hereinafter be described in further detail, the embodiment of orthodontic bracket assembly 150 of FIG. 3 has two arch wire contact surfaces 159 and 160 associated with attachment member 153. As seen in FIG. 1, after base member 152 and attachment member 153 have been movably associated with respect to one another, as will hereinafter be described in greater detail, arch wire receiving channel 155 is formed by the at least one arch wire contact surface 156 of base member 152 and the at least one arch wire contact surface 159 (FIGS. 1 and 2) or 159,160 (FIG. 3). The movable association means 154 includes a sliding connection means 161 between the base member 152 and the attachment member 153, wherein the sliding connection member means 161 includes an opening 162 disposed within the base member 152, and the attachment member 153 has an elongate support member 163 which is received within the opening 162 in a sliding relationship.

The elongate support member 163 of attachment member 153 preferably has a generally rectangular cross-sectional configuration having an upper end 164 having a rounded configuration as seen in FIGS. 1 and 3. Opening 162 in turn has the same generally rectangular cross-sectional configuration as that of the elongate support member 163 of attachment member 153, whereby the elongate support member 163 is slidable within opening 162, as well as guided within opening 162 by the wall surface 165 of base member 152 which forms opening 162. It should be apparent to one skilled in the art, that other cross-sectional configurations for elongate support member 163 and for the mating of opening 162 could be utilized in practicing the present invention.

Because of the sliding connection means 161 of the movable association means 154, different sizes of arch wire 151 can be accommodated within the arch wire receiving channel 155 of bracket assembly 150. Attachment member 153 may be moved with respect to base member 152 to either decrease the distance between arch wire contact surfaces 156 and 159 (or 159,160 as shown in FIG. 3) or to slide attachment member 153 downwardly to increase the distance between the arch wire contact surfaces 156 and 159 (or 159,160 in FIG. 3). Thus, if an orthodontist decides to change the size of the arch wire 151 being utilized in a particular orthodontic treatment, it is unnecessary to remove base member 152 from tooth 157, nor is it necessary for the orthodontist to remove and replace attachment member 153, in order to accommodate either a larger or smaller arch wire 151.

Still with reference to FIGS. 1-3, orthodontic bracket assembly 150 may be provided with a means for biasing 168 the base member 152 and the attachment member 153 together to bias the at least one arch wire contact surfaces 156,159,160 of the base member 152 and attachment member 153 into engagement with the arch wire 151. Conventional elastic bonds, or rubber bands, 169 (FIGS. 1-2 in phantom lines) may be utilized as the biasing means 168. The attachment member 153 and base member 152 may each be provided with wing members 170,171 associated therewith for engagement with the rubber band 169 in a conventional manner. Alternatively, base member 152 and attachment member 153 may be manufactured of a magnetic material, and/or magnetized, to provide the biasing means 168, whereby the base member 152 and the attachment member 153 are biased toward each other by the magnetic force of the magnetic material or the magnetic attraction forces between the base member 152 and attachment member 153. It should be noted that it is preferable that all the surfaces of the base member 152 and attachment member 153, including wing members 170,171 have a smooth rounded configuration so as to minimize any discomfort to the orthodontic patient.

With reference to FIGS. 1-4, orthodontic bracket assembly 150 of the present invention may include a means for releasably locking 175 the base member 152 and the attachment member 153 together while permitting the base member 152 and the attachment member 153 to move with respect to one another, whereby the base member 152 and the attachment member 153 are prevented from becoming accidentally disassociated while in use. For example, were a rubber band 169 to be used for the biasing means 168, and the rubber band 169 were to break, it would be possible that attachment member 153 could slide outwardly from base member 152, and either remain dangling from base member 152 or perhaps completely becoming disengaged therefrom. Releasable locking means 175 may be thus provided to the orthodontic bracket assembly 150. Releasable locking means 175, as seen in FIGS. 1-3, may include at least one projection member 176 disposed on attachment member 153 and engageable with the base member 152 to prevent the accidental disassociation of the base member 152 and the attachment member 153. The at least one projection member 176 of FIGS. 1-3 may be disposed upon the elongate support member 163 of attachment member 153, and the projection member 176 may have a rounded configuration which protrudes beyond the outer surface of elongate support member 163 and slightly beyond the opening 162 in base member 152. When it is desired to initially assemble bracket assembly 150 by inserting attachment member 153 within base member 152, there is sufficient yielding between attachment member 153 and base member 152, whereby the projection member 176 may be slightly compressed and pass through opening 162 of base member 152 and in turn pass wing 171 of base member 152, upon the application of sufficient force by the orthodontist. Were rubber band 169 to break, it is possible that attachment member 153 might slide downwardly, when viewed in FIG. 2; however, it is envisioned that an insufficient force would be exerted upon attachment member 153 to cause the projection member 176 to move past either wing 171 or through opening 162.

Figure 4:
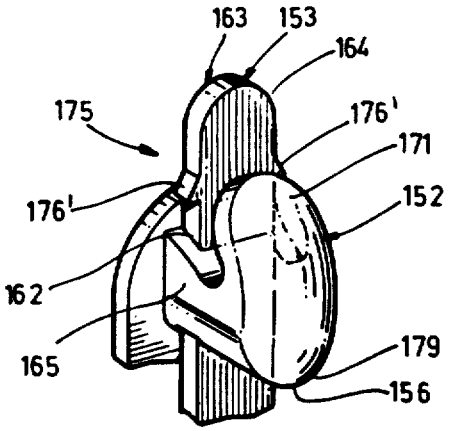
FIG. 4 is a partial perspective view of a portion of a bracket assembly in accordance with the present invention.

In FIG. 4, another embodiment of projection member 176 of locking means 175 is shown to comprise at least one, and preferably two tapered wedge members 176' which, upon the application of a sufficient force by the orthodontist, may pass through opening 162 and pass wall surface 165 of base member 152. Should biasing rubber band 169 break, it is believed that an insufficient force would be exerted upon the elongate support member 163, whereby the wedge members, or projection members, 176' would not pass through opening 162 in base member 152.

As seen in FIGS. 1-4, the arch wire contact surfaces 156,159,160, all have a rounded configuration 179. As seen in FIG. 1, when arch wire 151 is moved to the left or right is shown by arrows [180] *181*, arch wire 151 would not contact, nor engage, all of the arch wire contact surface 156 or 159, but rather would make point contact such as with line 180 or arch wire contact surface 159. Likewise, should arch wire 151 move in the direction shown by arrows 181, sliding movement of attachment member 153 with respect to base member 152 would accommodate movement of arch wire 151 in the direction of arrows 181, and arch wire 151 would likewise not contact the entire arch wire contact surface 156,159, although the surface area of arch wire contact surfaces 156 and 159 contacted by arch wire 151 would increase somewhat from that illustrated by line 181 of FIG. 1. Furthermore, as arch wire moves upwardly and downwardly in the direction shown by arrows 181, there are no sharp edges, such as right angle edges found in the prior art, which would grip, or bind, arch wire 151 within arch wire receiving channel 155.

With reference to FIG. 2, the orthodontic bracket assembly 150 may be provided with a means for torquing 185 the tooth 157 to which the base 152 is associated. As previously described, torquing of a tooth is twisting or turning of the tooth about an axis formed by the arch wire 151, or movement in the direction of arrows 186 in FIG. 2. Torquing means 185 may be provided by using an inclined surface 187 as at least one arch wire contact surface, which is preferably the arch wire contact surface 159' disposed upon attachment member 153. Because of the inclined surface 187 and its point contact with arch wire 151, bracket 150 may pivot about the point contact between arch wire 151 and the inclined surface 187 in the direction of arrows 186, dependent upon the forces acting upon bracket 150, which forces may be applied as by conventional ligature wires or rubber bands 169, attached to attachment member 153.

When bracket assembly is provided with torquing means 185, the arch wire contact surface 159', or inclined surface 187 (FIG. 2), is utilized. Arch wire contact surface 159' when viewed in the direction shown by arrow 188 in FIG. 1 would have the same rounded configuration 179 of arch wire contact surface 159 previously described, but the arch wire contact surface 159' would only lie in a plane as illustrated by phantom line 187, when viewed from the side as in FIG. 2.

The bracket assemblies 150 of FIGS. 1 and 3 are generally used for providing upward or downward movement of tooth 157 as will be hereinafter described in further detail with reference to FIGS. 5 and 6. Bracket assembly 150 of FIG. 2, when provided with torquing means 185, may be utilized to provide both upward or downward movement of tooth 157, as well as the torquing movement in the direction of arrows 186 as previously described. The embodiment of bracket assembly 150 of FIGS. 1-3 may also be utilized to provide rotation of tooth 157. Such rotation may be provided by disposing a shim or elastic band 190 (FIG. 2 in phantom lines) over wing members 170,171 and disposing the shim or elastic band 190 between the elongate support member 163 of attachment member 153 and the arch wire 151, with the rubber band 169 being used as biasing means 168 in the position shown in FIG. 2. Thus, the elastic band 190, or shim, permits tooth 157 to be rotated with respect to arch wire 151 about an axis formed by the longitudinal axis of elongate support member 163 of attachment member 153. As will be hereinafter further described in connection with FIG. 9, another manner in which to rotate tooth 157 will be described.

Figure 11:
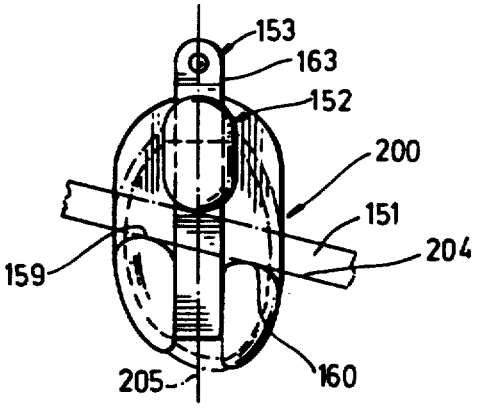
FIGS. 11 and 12 are front views of bracket assemblies in accordance with the present invention; for tipping movement of teeth associated with the bracket assemblies.
Figure 12:
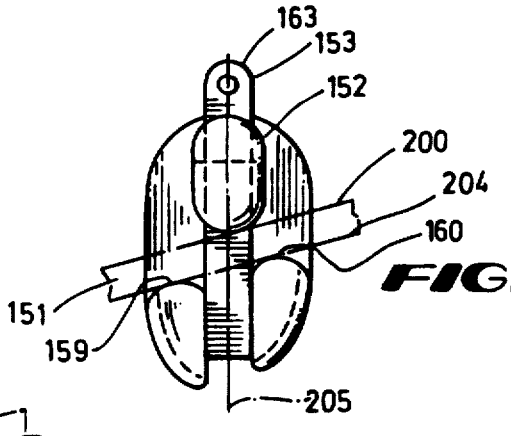

With reference now to FIGS. 5-6 and 11-12, a means for tipping 200 a tooth to which a base member 152 is associated will be described. In FIG. 5, tooth 157 is shown with the base member 152 and attachment member 153, as previously described in connection with FIG. 3, attached thereto. Biasing means 168 or rubber band 169 is utilized, and as seen in FIG. 6, upon completion of the orthodontic treatment, tooth 157 has been raised in the direction of arrow 201 to assume the position shown in FIG. 6. Tooth 202 of FIG. 5 is desired to be moved in the direction of arrow 203, or tipped in the direction of arrow 203 by the orthodontist. Means for tipping 200 tooth 202 includes two arch wire contact surfaces 159,160, as previously described in connection with FIG. 3, the two arch wire contact surfaces 159,160 being spaced apart from one another and disposed on the attachment member 153, as by connecting them to elongate support member 163 of attachment member 153, as previously described in connection with FIG. 3. The arch wire contact surfaces 159,160 of the bracket assembly 150 in FIG. 5 differ from those shown in FIG. 3 in that arch wire contact surfaces 159,160 lie in a plane 204 (phantom lines in FIG. 5 and as shown in FIGS. 11 and 12) which is not perpendicular with the longitudinal axis 205 of attachment member 153. Upon a biasing force being applied upon attachment member 153 and base member 152 as shown in FIG. 5, tooth 202 will pivot about arch wire contact surface 159 until tooth 202 assumes the orientation shown in FIG. 6, wherein both arch wire contact surfaces of attachment member 153 contact arch wire 151, as also seen in FIG. 11.

With reference to FIGS. 7 and 8, it is seen that it is desired to raise tooth 157 from position shown in FIG. 7 to that shown in FIG. 8, and it is desired to tip tooth 202 in the direction shown by arrow 203 into the position shown in FIG. 8. Likewise, it is desired to tip tooth 210 from the position shown in FIG. 7 to the position shown in FIG. 8. Tooth 210 is provided with a bracket assembly 150 having tipping means 200 wherein arch wire contact surfaces 160 and 159 are also disposed in the plane 204 which is not perpendicular with the longitudinal axis 205 of attachment member 153 as seen in FIGS. 7 and 12; however, in the case of the bracket assembly 150 associated with tooth 210, arch wire contact surface 160 is initially in contact with arch wire 151. After the biasing force has been applied, arch wire contact surface 159 of bracket assembly 150 will also contact arch wire 151, as shown in FIGS. 8 and 12. In FIGS. 7 and 8, tooth 220 is a molar, whereby it can be seen that through use of tipping means 202, it is possible to tip a tooth, such as tooth 201 mesially in the direction of arrow 203?, as well as to tip a tooth, such as tooth 210 distally as in the direction of arrow 204. As will be described in further detail in connection with FIGS. 13 and 14, molar 220 is provided with another embodiment of bracket assembly 150 which forms a buccal tube as will hereinafter be described in further detail.

Figure 10:
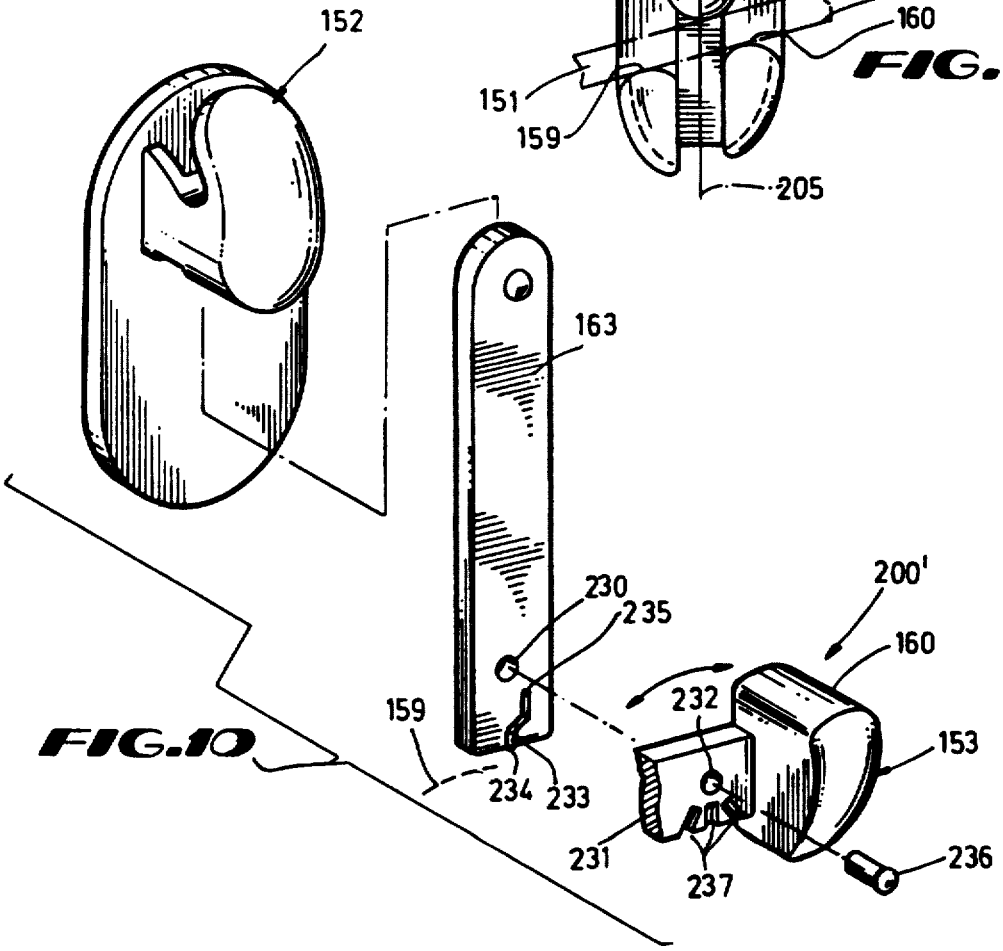
FIG. 10 is an exploded perspective view of a attachment member in accordance with the present invention.

With reference to FIG. 10, another tipping means 200' is illustrated. Whereas the tipping means 200 is shown in FIGS. 5–7 and 11–12 utilizes two arch wire contact surfaces which are fixedly secured to the attachment member 153, in FIG. 10 the two arch wire contact surfaces 159,160 are adjustably mounted on the attachment member 153. As seen in FIG. 10, elongate support member 163 is provided with an opening 230, and arch wire contact surfaces 159,160 (arch wire contact surface 159 being shown in phantom lines) are disposed apart from another via a connector member 231 having an opening 232 form therein. The lower end of elongate support member 163 has a tension wire, or spring, 233 having its lower end 234 fixedly secured to the lower end of elongate support member 163. The upper end 235 of tension wire, or spring, 233 is spaced outwardly from elongate support member 163. Connector member 231 is then disposed between the upper end 235 of tension wire spring 233 and elongate support member 163, with opening 232 of connector member 231 in a mating relationship with opening 234 of elongate support member 163. A pin or screw connector 236 may then be passed through openings 232 into opening 230 to secure connector member 231 to elongate support member 163. The upper end 235 of tension wire, or spring, 233 may then be engageable with a plurality of slotted grooves 237 formed in connector member 231. By turning the connector member 231 with arch wire contact surfaces 159,160 attached thereto, about pin 236, the upper end 235 of tension wire or spring 233 will mate with one of the grooves 237, whereby arch wire contact surfaces may assume the positions shown in FIGS. 11, 12, or 3, dependent upon which groove the upper end 235 of tension wire or spring 233 is disposed.

Figure 9:
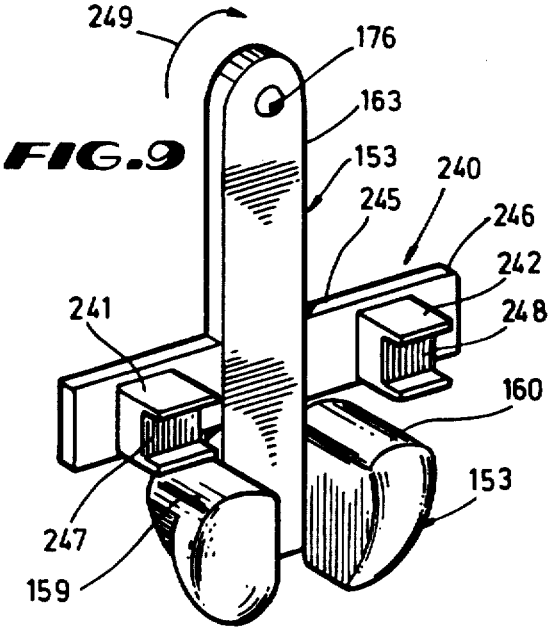
FIG. 9 is a perspective view of an attachment member in accordance with the present invention.

With reference now to FIG. 9, a means for rotating 240 a tooth to which a base member 152 (FIG. 3) is associated, is illustrated. Attachment member 153 of FIG. 9 is identical to that previously described in connection with FIG. 3 and is used with the same base member 152 as previously described in connection with FIGS. 1–8 and 10–12, with the exception that base member 153 is provided with rotation means 240. Rotation means 240 includes at least one arch wire support block 241,242 disposed on attachment member 153 and adjacent the at least one arch wire contact surface 159,160. The arch wire support blocks 241,242 may be fixedly secured to attachment member 153 as by a cross member 245 fixedly secured to the elongate support member 163 of attachment member 153. When the attachment member 153 of FIG. 9, having rotation means 240 associated therewith, is disposed on base member 152, arch wire 151 will abut and contact the arch wire support blocks 241,242, which in turn provides a fulcrum for the tooth to be rotated about its longitudinal axis. If a single arch wire support block 241 is utilized as the rotation means 240, this arch wire support block 241 would contact the arch wire 151, upon application of a biasing force, such as by a rubber band connecting end 246 of cross member 245 to arch wire 151. That biasing force will cause the tooth to rotate about the contact point between arch wire support block 241 and arch wire 151, or in other words will cause the tooth to be rotated about its longitudinal axis, which would generally correspond to the longitudinal axis of the attachment member 153. If two arch wire support blocks 241,242 were utilized as the rotation means 240, each arch wire support block would have a groove 247,248 formed therein to matingly receive arch wire 151. The depth of the two grooves 247,248 would differ whereby at the beginning of the treatment, the arch wire would only be in contact with the bottom of one of the grooves, the other groove bottom being spaced from the arch wire. After application of a biasing force upon attachment member 153, the tooth will be rotated whereby both groove bottoms would be in contact with arch wire 151. For example, if the groove 248 of arch wire support block 242 were deeper than the groove 247 of arch wire support block 241, only the bottom of groove 247 of arch wire support block 241 would contact arch wire 151. Upon application of a biasing force, upon the end 246 of cross member 245, a tooth associated with attachment member 153 of FIG. 9 would be rotated in the direction shown by arrow 249. Rotation in the opposite direction from arrow 249 could be achieved by reversing the arch wire support blocks 241,242. It should be noted that the rotation means 240 illustrated in FIG. 9 could be combined with tipping means 200, by disposing arch wire contact surfaces 159,160 in a plane which is not perpendicular with the longitudinal axis of the attachment member 153 as previously described in connection with FIGS. 5–8 and 10–12.

Figure 13:
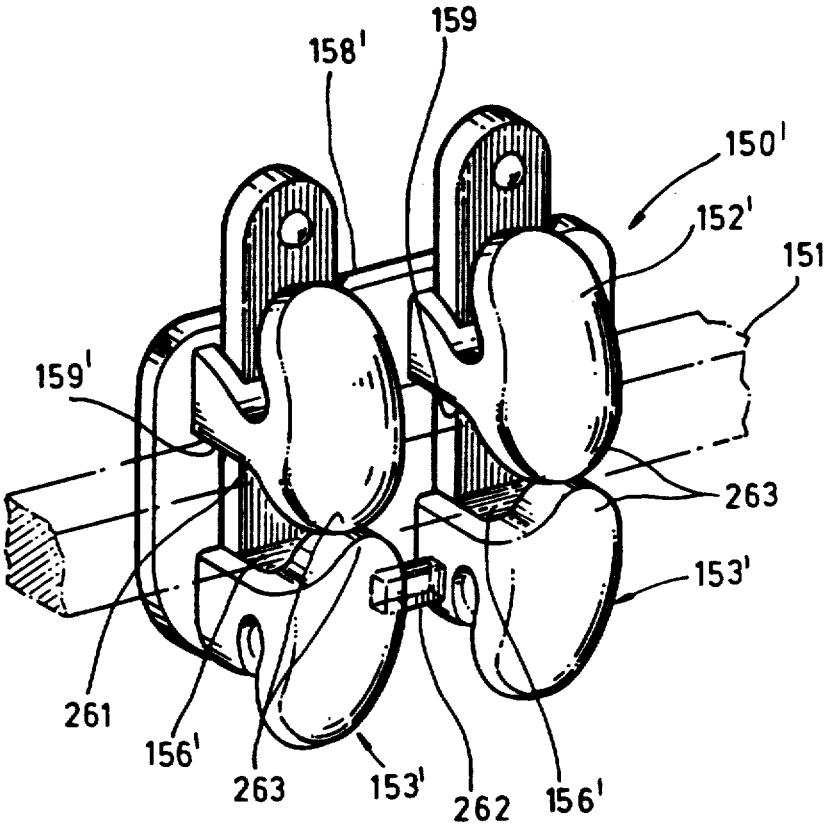
FIG. 13 is a perspective view of a bracket assembly in accordance with the present invention when a buccal tube is provided.
Figure 14:
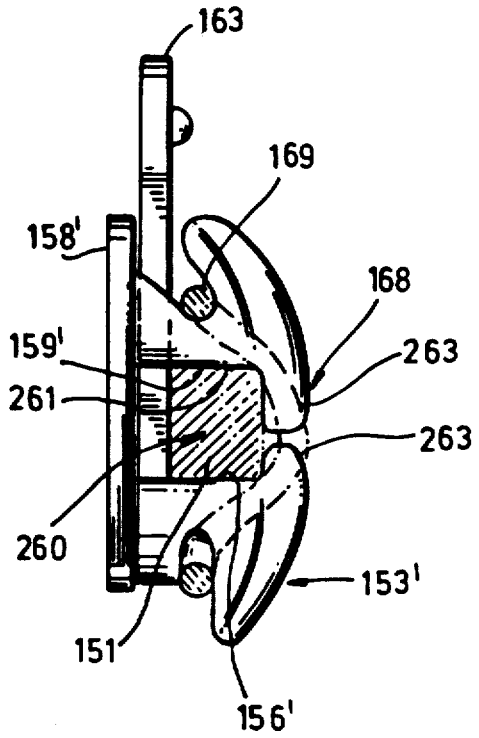
FIG. 14 is a side view of the bracket assembly of FIG. 13.

With reference now to FIGS. 13 and 14, a buccal tube 260 embodiment of bracket assembly 150' is illustrated. A base member 152' is provided which has two arch wire contact surfaces 159' associated with mounting base 158'. Mounting base 158' differs from mounting base 158 previously described in that it is wider to accommodate the two arch wire contact surfaces 156'. Arch wire contact surfaces 159' differ from those previously described in connection with FIG. 1, in that arch wire contact surfaces 159' do not have a rounded configuration, but rather a flat planer configuration 261, as found in conventional buccal tubes. Bracket assembly 150' is provided with two attachment member 153' as previously described in connection with FIG. 1, with the exception that arch wire contact surfaces 159' have the same configuration as contact surfaces 156' as previously described. If desired, the two attachment members 153' could be joined by a connector member 262 as shown in phantom lines in FIG. 13 to provide additional strength and rigidity. Each arch wire contact surface 159' and 156' is provided with enclosure member 263 disposed adjacent each arch wire contact surface. As seen in FIGS. 13 and 14, biasing means 168 or rubber bands 169 cause the attachment members 153' to move into an abutting relationship with the base member 152' whereby the closure members 267 of the attachment member 153' abut the closure members 267 of the base member 152' to form a buccal tube 260 which receives the arch wire 151 therein. As is conventional in the art, buccal tubes 260 are typically provided upon molars, such as molar 220 (FIGS. 7 and 8).

In accordance with the invention, as previously described, a method for forming a variable sized arch wire receiving channel 155 in an orthodontic bracket assembly 150 comprises the steps of: (a) providing at least one arch wire contact surface 156 upon a base member 152; (b) providing at least one arch wire contact surface 159 upon movement member 153; and (c) movably associating the base member 152 and the attachment member 153 with respect to one another, whereby the at least one arch wire contact surfaces 156,159 of the base member 152 and the attachment member 153 may contact and engage the arch wire 151. As previously described, a further step of the method in accordance with the present invention is movably associating the attachment member 153 and the base member 152 with respect to one another by slidably receiving a portion of the attachment member 153, such as elongate support arm 163, within an opening 162 formed in the base member 152.

It should be noted that in beginning an orthodontic treatment with the adjustable orthodontic bracket assembly 150 of the present invention, a base member may be initially bonded to all the teeth, but it is not necessary to use an attachment member in connection with each base member. For example, initially there may be a tooth which is disposed so far away from the arch wire that an attachment member would not reach the particular base member with which it should be associated. With the adjustable orthodontic bracket assembly of the present invention, the attachment member 153 can be deleted and a biasing means, or rubber band, can be stretched between the base member and the arch wire, or between the base member and an adjacent tooth to initially move the malposed tooth into its proper orientation. While the attachment is not being utilized, it does not interfere with the treatment of adjacent teeth, and after the malposed tooth has moved toward its desired orientation, an attachment member can be later associated with the base member in the manner previously described herein.

It is to be understood that the invention is not limited to the exact details of construction, operation, exact materials, or embodiment shown and described, as obvious modifications and equivalents will be apparent to one skilled in the art. For example, while the adjustable orthodontic bracket assembly of the present invention has been illustrated for use on the labial and buccal surfaces of the teeth, the bracket assembly of the present invention could be used on the lingual surfaces of the teeth. Accordingly, the invention is therefore to be limited only by the scope of the appended claims.

I claim:

1. An adjustable orthodontic bracket assembly adapted for use with an arch wire comprising:

a base member having at least one arch wire contact surface, the base member adapted to be associated with the surface of a tooth, the tooth having a longitudinal axis;

an attachment member having at least one arch wire contact surface; [and]

means for movably associating the base member and the attachment member with respect to one another, along an axis substantially parallel to the longitudinal axis of the tooth, to provide an arch wire receiving channel formed by the at least one arch wire contact surfaces of the base member and the attachment member, whereby the size of the arch wire receiving channel may be varied to accommodate different sizes of arch wire by relative movement between the base member and the attachment member *; and*

*means for biasing the base member and the attachment member together to bias the at least one arch wire contact surface of the base member and the attachment member into engagement with the arch wire.*

2. The adjustable orthodontic bracket assembly of claim 1, wherein the movable association means includes a sliding connection means between the base member and the attachment member.

3. The adjustable orthodontic bracket assembly of claim 2, wherein the sliding connection means includes an opening disposed within the base member and the attachment member has an elongate support member which is received within the opening in a sliding relationship.

[4. The adjustable orthodontic bracket assembly of claim 1, including means for biasing the base member and the attachment member together to bias the at least one arch wire contact surfaces of the base member and the attachment member into engagement with the arch wire.]

5. The adjustable orthodontic bracket assembly of claim [4] *1*, wherein the biasing means comprises a rubber band which is associated with the attachment member and the base member.

6. The adjustable orthodontic bracket assembly of claim 5, wherein the attachment member and the base member each have a wing member associated therewith which engages with the rubber band.

7. The adjustable orthodontic bracket assembly of claim [4] *1*, wherein the base member and the attachment member are magnetized to provide the biasing means whereby the base member and the attachment member are biased toward one another by magnetic force.

8. The adjustable orthodontic bracket assembly of claim 1, including a means for releasably locking the base member and the attachment member together while permitting the base member and the attachment member to move with respect to one another, whereby the base member and the attachment member are prevented from becoming accidentally disassociated while in use.

9. The adjustable orthodontic bracket assembly of claim 8, wherein the releasable locking means includes at least one projection member disposed on the attachment member, the at least one projection member being engageable with the base member to prevent accidental disassociation of the base member and the attachment member.

10. The adjustable orthodontic bracket assembly of claim 3, including a means for releasably locking the base member and the attachment member together while permitting sliding movement of the attachment member with respect to the base member, the releasable locking means including at least one projection member disposed on the elongate support member of the attachment member, the at least one projection member being engageable with the base member adjacent the opening formed in the base member.

11. The adjustable orthodontic bracket assembly of claim 1, wherein the at least one arch wire contact surfaces of the base member and the attachment member have a rounded configuration, whereby binding of the arch wire within the arch wire receiving channel is minimized.

12. The adjustable orthodontic bracket assembly of claim 1, including means for tipping the tooth to which the base member is associated, the tipping means including two arch wire contact surfaces spaced apart from one another and disposed on the attachment member, the two arch wire contact surfaces lying in a plane which is not perpendicular with the longitudinal axis of the attachment member, whereby the tooth may be tipped about the at least one arch wire contact surface of the base member and one contact surface of the attachment member until both arch wire contact surfaces of the attachment member contact the arch wire.

13. The adjustable orthodontic bracket assembly of claim 12, wherein the two arch wire contact surfaces on the attachment member are fixedly secured to the attachment member.

14. The adjustable orthodontic bracket assembly of claim 12, wherein the two arch wire contact surfaces on the attachment member are adjustably mounted on the attachment member.

15. The adjustable orthodontic bracket assembly of claim 1, including means for rotating the tooth to which the base member is associated, the rotation means including at least one arch wire support block disposed on the attachment member and adjacent the at least one arch wire contact surface, the arch wire support block adapted to contact the arch wire and provide a fulcrum about which the tooth is rotated.

16. The adjustable orthodontic bracket assembly of claim 1, wherein two arch wire contact surfaces are disposed on the base member and spaced apart from one another; two arch wire contact surfaces are disposed on the attachment member and spaced apart from one another; and a closure member is disposed adjacent each arch wire contact surface, the closure members of the attachment member abutting the closure members of the base member, whereby a buccal tube is provided and adapted to receive the arch wire therein.

17. The adjustable orthodontic bracket assembly of claim 1, including means for torquing the tooth to which the base member is associated, the torquing means being formed by an inclined surface used as at least one arch wire contact surface.

18. The adjustable orthodontic bracket assembly of claim 17, wherein the inclined surface is disposed on the at least one arch wire contact surface of the attachment member.

19. A method for forming a variable sized arch wire receiving channel in an orthodontic bracket assembly comprising the steps of:

(a) providing at least one arch wire contact surface upon a base member adapted to be associated with a tooth having a longitudinal axis;

(b) providing at least one arch wire contact surface upon an attachment member; [and]

(c) movably associating the base member and the attachment member with respect to one another along an axis substantially parallel to the longitudinal axis of the tooth, whereby the at least one arch wire contact surfaces of both base member and the attachment member may contact and engage the arch wire *; and*

*biasing the base member and the attachment member together to bias the at least one arch wire contact surfaces of the base member and the attachment member into engagement with the arch wire.*

20. The method of claim 19, wherein the attachment member and the base member are movably associated with respect to one another by slidably receiving a portion of the attachment member within an opening formed in the base member.

*21. An orthodontic edgewise bracket assembly for use on labial and buccal surfaces of a tooth and adapted for use with an arch wire comprising:*

*a base member having a mounting base for bonding to the labial or buccal surface of a tooth, the tooth having a longitudinal axis;*

*two or three arch wire contact surfaces associated with the base member and spaced from each other along the longitudinal axis of the tooth to provide an arch wire receiving channel formed by at least two arch wire contact surfaces, the arch wire contact surfaces lying in planes which are substantially perpendicular to the longitudinal axis of the tooth and to the labial or buccal surface of the tooth; and each arch wire contact surface having a rounded configuration, without sharp edges which contact the arch wire and cause the arch wire to bind within the arch wire receiving channel, whereby the arch wire does not contact all of the arch wire contact surfaces and binding of the arch wire within the arch wire receiving channel is prevented.*

*22. The orthodontic bracket assembly of claim 21, wherein each rounded arch wire contact surface slopes away from a portion of each arch wire contact surface which contacts the arch wire.*

* * * * *